United States Patent
Hofer et al.

(10) Patent No.: US 10,555,662 B2
(45) Date of Patent: Feb. 11, 2020

(54) IMAGE RECORDING APPARATUS, METHOD FOR CONFIGURING A CAMERA HEAD OF AN IMAGE RECORDING APPARATUS AND IMAGE RECORDING APPARATUS SET

(71) Applicant: Scholly Fiberoptic GmbH, Denzlingen (DE)

(72) Inventors: Axel Hofer, Endingen (DE); Wolfgang Endress, VS-Schwenningen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 176 days.

(21) Appl. No.: 15/216,095

(22) Filed: Jul. 21, 2016

(65) Prior Publication Data
US 2017/0020364 A1    Jan. 26, 2017

(30) Foreign Application Priority Data
Jul. 23, 2015   (DE) ........................ 10 2015 009 507

(51) Int. Cl.
| | | |
|---|---|---|
| *A61B 1/04* | (2006.01) | |
| *H04N 5/225* | (2006.01) | |
| *H04N 7/18* | (2006.01) | |
| *A61B 1/00* | (2006.01) | |
| *A61B 1/045* | (2006.01) | |
| *A61B 90/98* | (2016.01) | |

(52) U.S. Cl.
CPC ........ *A61B 1/0002* (2013.01); *A61B 1/00009* (2013.01); *A61B 1/045* (2013.01); *A61B 90/98* (2016.02); *A61B 1/00016* (2013.01); *A61B 1/00059* (2013.01); *H04N 2005/2255* (2013.01)

(58) Field of Classification Search
CPC ... A61B 1/0002; A61B 90/98; A61B 1/00059; A61B 1/00018; A61B 1/00009; A61B 1/053; A61B 1/045; A61B 1/00016; H04N 5/23229; H04N 2005/2255
USPC .......................................................... 348/75
See application file for complete search history.

(56) References Cited

U.S. PATENT DOCUMENTS

| | | | |
|---|---|---|---|
| 5,896,166 A * | 4/1999 | D'Alfonso | A61B 1/0002 348/72 |
| 7,520,853 B2 | 4/2009 | Amling et al. | |
| 7,855,727 B2 * | 12/2010 | Adler | A61B 1/045 348/211.14 |
| 8,982,202 B2 | 3/2015 | Saito et al. | |
| 2004/0028390 A9 | 2/2004 | Chatenever et al. | |
| 2008/0183981 A1 | 1/2008 | Tannai | |
| 2014/0142383 A1 * | 5/2014 | Blumenzweig | A61B 1/00105 600/110 |

(Continued)

FOREIGN PATENT DOCUMENTS

| | | |
|---|---|---|
| JP | 2005065871 | 3/2005 |
| JP | 2012248029 | 12/2012 |

*Primary Examiner* — Susan E. Hodges
(74) *Attorney, Agent, or Firm* — Volpe and Koenig, P.C.

(57) ABSTRACT

An arrangement of an image recording apparatus 1 with a storage device (9) on a side of an interface (8) with a camera control unit (2) that faces the camera head (3) and for implementing in the camera control unit (2) a configuration unit (10) with which camera-head-specific information is readable from the storage device (9) and transmittable to an image signal pre-processing unit (4) of the camera head (3) for configuration.

13 Claims, 3 Drawing Sheets

(56) References Cited

U.S. PATENT DOCUMENTS

| | | | |
|---|---|---|---|
| 2014/0184764 A1* | 7/2014 | Amling | A61B 1/00105 |
| | | | 348/65 |
| 2014/0320684 A1* | 10/2014 | Chatenever | H04N 5/23225 |
| | | | 348/211.4 |
| 2015/0199603 A1* | 7/2015 | Troeger | H01Q 1/2225 |
| | | | 235/492 |

* cited by examiner

IMAGE RECORDING APPARATUS, METHOD FOR CONFIGURING A CAMERA HEAD OF AN IMAGE RECORDING APPARATUS AND IMAGE RECORDING APPARATUS SET

INCORPORATION BY REFERENCE

The following documents are incorporated herein by reference as if fully set forth: German Patent Application No. 102015009507.2, filed Jul. 23, 2015.

FIELD OF THE INVENTION

The invention relates to an image recording apparatus having a camera head control unit and a camera head, wherein the camera head has an image signal pre-processing unit for generating an image signal stream, and the camera control unit has an image signal processing unit, and wherein the camera head is releasably connectable to the image signal processing unit via an interface for transmitting the image signal stream.

The invention furthermore relates to a method for configuring a camera head of an image recording apparatus, wherein a camera control unit is connected to the camera head and reads camera-head-specific information.

The invention finally relates to an image recording apparatus set having a camera control unit and at least two camera heads.

BACKGROUND

It is known to equip endoscope arrangements with an image sensor that records an image of an examination area and converts it into an electrical signal. In order to make the electrical signals available for further digital processing, it has become customary to implement an image signal pre-processing unit in a camera head, which can contain the image sensor or is connectable to an image sensor—for example arranged in an endoscope tip. In order to adapt an image recording apparatus thus created to specific application cases, it has become customary to produce different camera heads for example having different image sensors or for different endoscope shafts. The camera heads are each connected to a camera control unit here, which, among others, brings the transmitted signals into a form which is displayable on a monitor.

It is necessary here for the camera control unit to be adapted to the conditions of the camera head or, vice versa, to match the camera head to the camera control unit.

For preparing the endoscope or the camera head after use, it has become customary to detach the camera head from the camera control unit. To this end, an interface is implemented, via which the camera head is detachably connectable to the camera control unit.

SUMMARY

The invention is based on the object of improving the use properties of an image recording apparatus.

One or more features according to the invention are provided to achieve this object. In particular, according to the invention for achieving said object an image recording apparatus of the type described in the introduction is provided with a storage device containing camera-head-specific information to be connectable via the interface to a configuration unit in the camera control unit, and for the configuration unit to be set up for receiving the camera-head-specific information from the connected storage device and for reading configuration data, corresponding to the camera-head-specific information, from a configuration data storage device of the camera control unit, and for the camera control unit to be set up for configuring the image signal pre-processing unit with the configuration data. What is advantageous here is that independent adaptation of the camera head to the camera control unit or setting up of the camera head is achievable. The arrangement of the camera-head-specific information in a storage device that is assigned to the camera head according to the invention here offers the advantage that the camera head is identifiable by the camera control unit without error, in particular without additional inputs by a user. The arrangement or provision of the configuration data necessary for adapting the camera head in the camera control unit according to the invention offers the advantage that the storage device in the camera head can be designed with less storage capacity and the configuration data are updatable and modifiable independently of the camera head. This can be an advantage for example if the configuration data refer to a multiplicity of different, yet for example structurally identical, camera heads. The invention thus improves handling of the image recording apparatus and thus the use properties thereof. The configuration unit is here preferably set up for configuring the image signal pre-processing unit with the configuration data. The configuration can here be done directly or indirectly, for example via the image signal processing unit.

The image signal pre-processing unit can be or comprise, for example, an FPGA unit, a microcontroller, a CPLD (complex programmable logic device) unit and/or a combination of an FPGA unit and a microcontroller.

In one embodiment of the invention, provision may be made for the interface to be implemented at a connecting cable. What is advantageous here is that disturbance-free transmission of the image signal stream can be carried out.

In one embodiment of the invention, provision may be made for the storage device to be arranged at or in a connection of the interface. Advantageous is here that no further connecting steps for reading the storage device are necessary, because the storage device, with connection of the interface, is readable by the camera control unit. In particular, provision may be made here for the connection to be implemented at a plug. This permits simple connection via the interface. Provision is preferably made here for the plug to be implemented at an end of the connecting cable that faces the camera control unit. This has the advantage that the storage device is arranged as closely as possible to the camera control unit.

In one embodiment of the invention, provision may be made for the storage device to be readable in a wire-connected fashion. Advantageous is here that disturbance-free reading of the storage device is achievable. Provision may alternatively or additionally be made for the storage device to be readable in a wireless fashion. The advantage here is that electrical contacts for reading the storage device can be omitted. Provision may be made here for example for the storage device to have an RFID transponder. It is particularly expedient here if the storage device is arranged at an end of the connecting cable that faces the camera control unit.

In one embodiment of the invention, provision may be made for the configuration data to comprise at least one look-up table. Advantageous is here that converting the camera-head-specific information to associated configuration data is easily achievable. Alternatively or additionally, the configuration data can comprise at least one short code. The advantage here is that addressing configuration data which are to be provided to the image signal pre-processing unit is easily achievable. By way of example, the short code can correspond to the camera-head-specific information and/or trigger a command sequence during configuration.

In one embodiment of the invention, provision may be made for the configuration unit to be set up for writing the configuration data to the image signal pre-processing unit. The advantage here is that means for administrating the configuration of the image signal pre-processing unit in the camera head can be omitted. Provision is preferably made here for the configuration unit to be set up for direct writing of the configuration data to the image signal pre-processing unit. The complexity in terms of apparatus in the camera head can thus be kept low.

In one embodiment of the invention, provision may be made for updating means for updating configuration data in the configuration data storage means to be implemented and set up in the camera control unit. The advantage here is that updating the configuration data can be carried out independently of the camera head. Provision is preferably made here for the updating means to be implemented and set up for updating if the camera head is separate from the camera control unit. This allows the aforementioned updating for a multiplicity of camera heads to be carried out in one updating process in a simple manner, without requiring that the camera heads are connected in each case.

For achieving this object, additional features directed to a method, are provided in a method for configuring a camera head of an image recording apparatus according to the invention. In particular, in a method of the type described in the introduction for achieving said object, it is provided according to the invention, with respect to the camera-head-specific information, for configuration data corresponding to the camera-head-specific information to be read from a configuration data storage means of the camera control unit and to be transmitted to the camera head, and for the configuration data to be used for setting up an image signal pre-processing unit of the camera head. The invention thus makes possible the administrative control over the configuration data in the camera control unit. Administration and updating of configuration data is thus achievable for a multiplicity of camera heads equally. In addition, the invention allows for the camera head and the camera control unit to be automatically adapted to one another, in particular in the case of or by connecting via an interface. The use properties of an image recording apparatus can be hereby improved.

In one embodiment of the invention, provision may be made for the configuration data to be read with a configuration unit of the camera control unit and to be transmitted to the camera head. The advantage here is that controlling of a configuration process can be carried out by the camera control unit. The computational complexity in the camera head can thus be reduced or be kept low.

In one embodiment of the invention, provision may be made for the camera-head-specific information to be read in a wire-connected fashion. Disturbances by external radio disturbance signals are thus simply avoidable. Provision may alternatively or additionally be made for the camera-head-specific information to be read in a wireless fashion. This permits contactless transmission of the camera-head-specific information.

In one embodiment of the invention, provision may be made for at least one look-up table to be used as the configuration data. A look-up table allows simple provision of configuration data that are associated with the transmitted camera-head-specific information. Provision may alternatively or additionally be made for at least one short code to be transmitted as the configuration data. The advantage here is that the short code can be transmitted to the camera head, which derives herefrom associated configuration steps for the image signal pre-processing unit. The short code can also be converted by the configuration unit into configuration steps.

In one embodiment of the invention, provision may be made for the image signal pre-processing unit to be configured by the configuration unit. This can be done, for example, via the already mentioned short codes and/or directly, for example by writing the configuration data to the image signal pre-processing unit without further processing or conversion in the camera head.

In one embodiment of the invention, provision may be made for the configuration data in the configuration data storage device to be updated. The advantage here is that updating the configuration data can be carried out for all connectable camera heads equally. It is thus possible, for example, in a simple manner to prevent that, if a camera head fails and a further camera head that is kept in reserve is connected, it transpires that the further camera head cannot cooperate with the camera control unit because the camera head unit is too new or is otherwise not compatible with the camera head.

In one embodiment of the invention, provision may be made for the image recording apparatus to be used with an FPGA unit, a microcontroller, a CPLD unit and/or a combination of an FPGA unit and a microcontroller as the image signal pre-processing unit.

It is particularly expedient if the method according to the invention is used with an image recording apparatus according to the invention, especially as described above and/or as claimed in one of the claims that are directed at an image recording apparatus.

The invention is thus advantageously usable in an image recording apparatus set having a camera control unit and at least two camera heads, wherein each of the at least two camera heads forms with the camera control unit an image recording apparatus according to the invention, in particular as described above and/or as claimed in one of the claims that are directed at an image recording apparatus, and/or wherein a method according to the invention, in particular as already described and/or as claimed in one of the claims that are directed at a method, can be carried out with each of the at least two camera heads and the camera control unit.

BRIEF DESCRIPTION OF THE DRAWINGS

The invention will now be described in more detail with reference to exemplary embodiments, but is not limited to said exemplary embodiments. Further exemplary embodiments can be gathered from a combination of the features of individual or multiple claims of protection and/or with individual or several features of the exemplary embodiments.

For explaining the invention in greatly simplified illustration.

DETAILED DESCRIPTION OF THE PREFERRED EMBODIMENT

Figure 1:
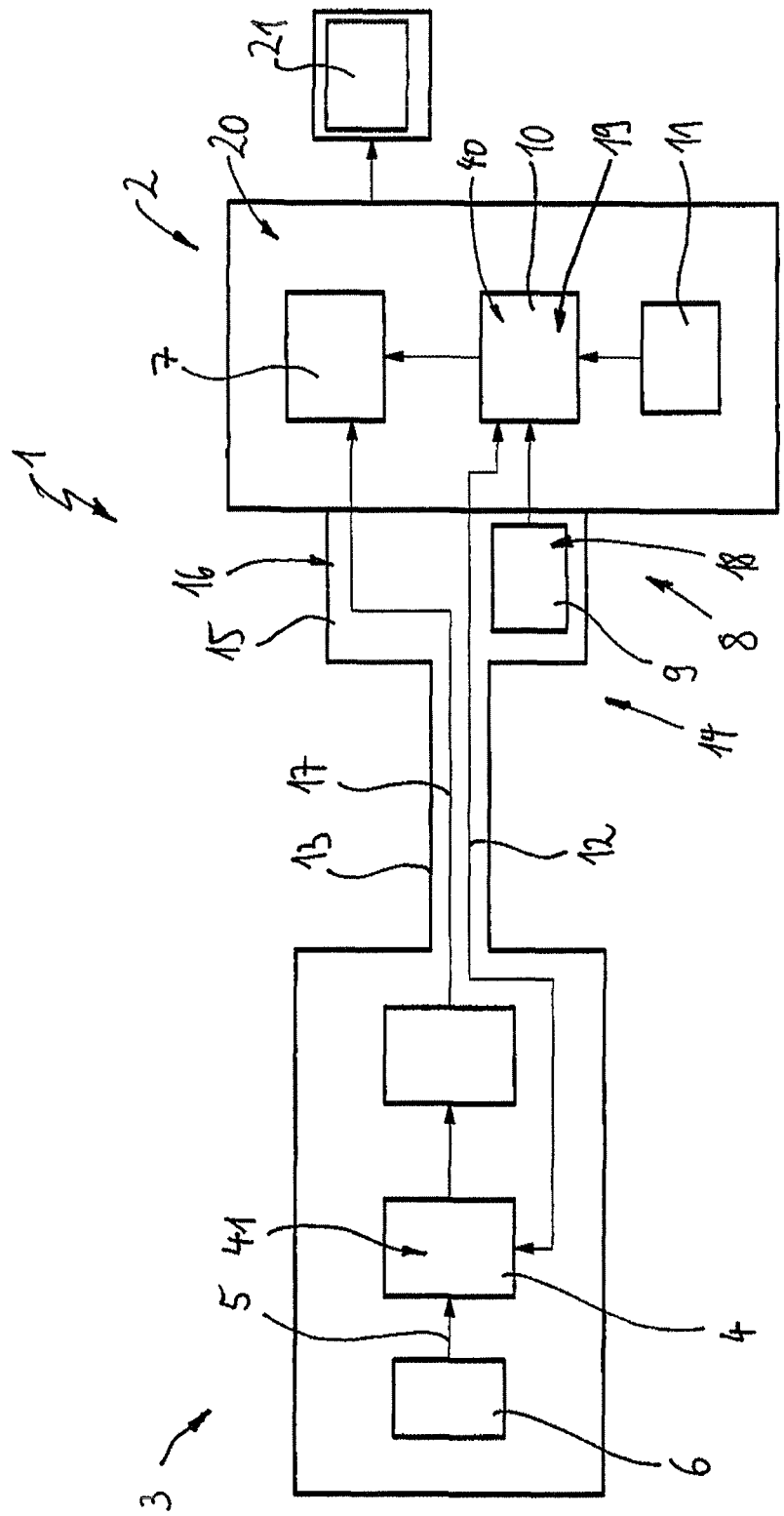
FIG. 1: shows an image recording apparatus according to the invention, in which an image sensor is integrated in the camera head.

FIG. 1 shows a block diagram of an image recording apparatus according to the invention that is designated 1 as a whole.

The image recording apparatus 1 has a camera control unit 2 and a camera head 3.

Arranged in the camera head 3 is an image signal pre-processing unit 4. The image signal pre-processing unit 4 is set up in a manner known per se for generating an image signal stream from electrical signals 5 of an image sensor 6. For explaining the exemplary embodiment, the image signal pre-processing unit 4 is here an FPGA unit 41.

The camera control unit 2 has an image signal processing unit 7. The image signal processing unit 7 is set up in a manner known per se for preparing the image signal stream from the image signal pre-processing unit 4. To this end, the image signal processing unit 7 can for its part have a corresponding FPGA (field programmable gate array).

An interface 8, by which the camera head 3 is detachably connectable for transmitting the image signal stream to the image signal processing unit 7 of the camera control unit, is implemented between the camera control unit 2 and the camera head 3. A storage device 9 or memory, in which camera-head-specific information for identifying the connected camera head 3 is provided, is implemented on the camera-head-side of this interface 8.

The storage device 9 is connectable via the interface 8 to a configuration unit 10 of the camera control unit 2.

The camera-head-specific information is thus transmittable to the camera control unit 2 and receivable by the configuration unit 10.

Furthermore implemented in the camera control unit 2 is a configuration data storage device 11 or memory, in which configuration data that correspond to the camera-head-specific information are provided.

The configuration unit 10 is set up such that configuration data that correspond to camera-head-specific information, which the configuration unit 10 has obtained from the storage device 9, are readable and read from the configuration data storage device 11. The configuration unit 10 has a microprocessor 40 (not illustrated further) to this end.

The configuration unit 10 is furthermore set up for configuring the image signal pre-processing unit 4 in the camera head 3 with said read configuration data via a data link 12.

The interface 8 is implemented at a connecting cable 13. To this end, a connection 15 of the interface 8 is implemented at the end 14 of the connecting cable that is remote from the camera head 3 and thus facing the camera control unit. The storage device 9 is arranged in this connection 15.

In the exemplary embodiment, the connection 15 is a plug 16, which electrically connects the data link 12 and a transmission channel 17 for the image data stream to the camera control unit 2.

The storage device 9 is here not electrically connected to the configuration unit 10, but is read wirelessly. The storage device here has an RFID transponder 18 (not illustrated further) that is known per se, and the configuration unit 10 has an RFID reader 19 (also not illustrated further) that is known per se.

Stored in the configuration data storage device 11 is a look-up table with which the received camera-head-specific information is convertible to configuration data. The configuration data here comprise short codes with which the configuration of the image signal pre-processing unit 4 is controllable.

The configuration unit 10 is here set up for direct writing of said configuration data to the image signal pre-processing unit 4. Alternatively or additionally, the configuration unit 10 can be setup for indirectly writing said configuration data to the image signal pre-processing unit 4 via the image signal processing unit 7.

Furthermore implemented in the camera control unit 2 are updating means 20 with which the configuration data in the configuration data storage device 11 can be updated. Here, the camera control unit 2 has, for example, means for establishing an Internet connection or another data link independently of whether or not a camera head 3 is connected to obtain the updated configuration data and to write them to the configuration data storage device 11.

The image data stream received by the transmission channel 17 is processed after configuration of the image signal pre-processing unit 4 in the image signal processing unit 7 and displayed on a monitor 21.

Figure 2:
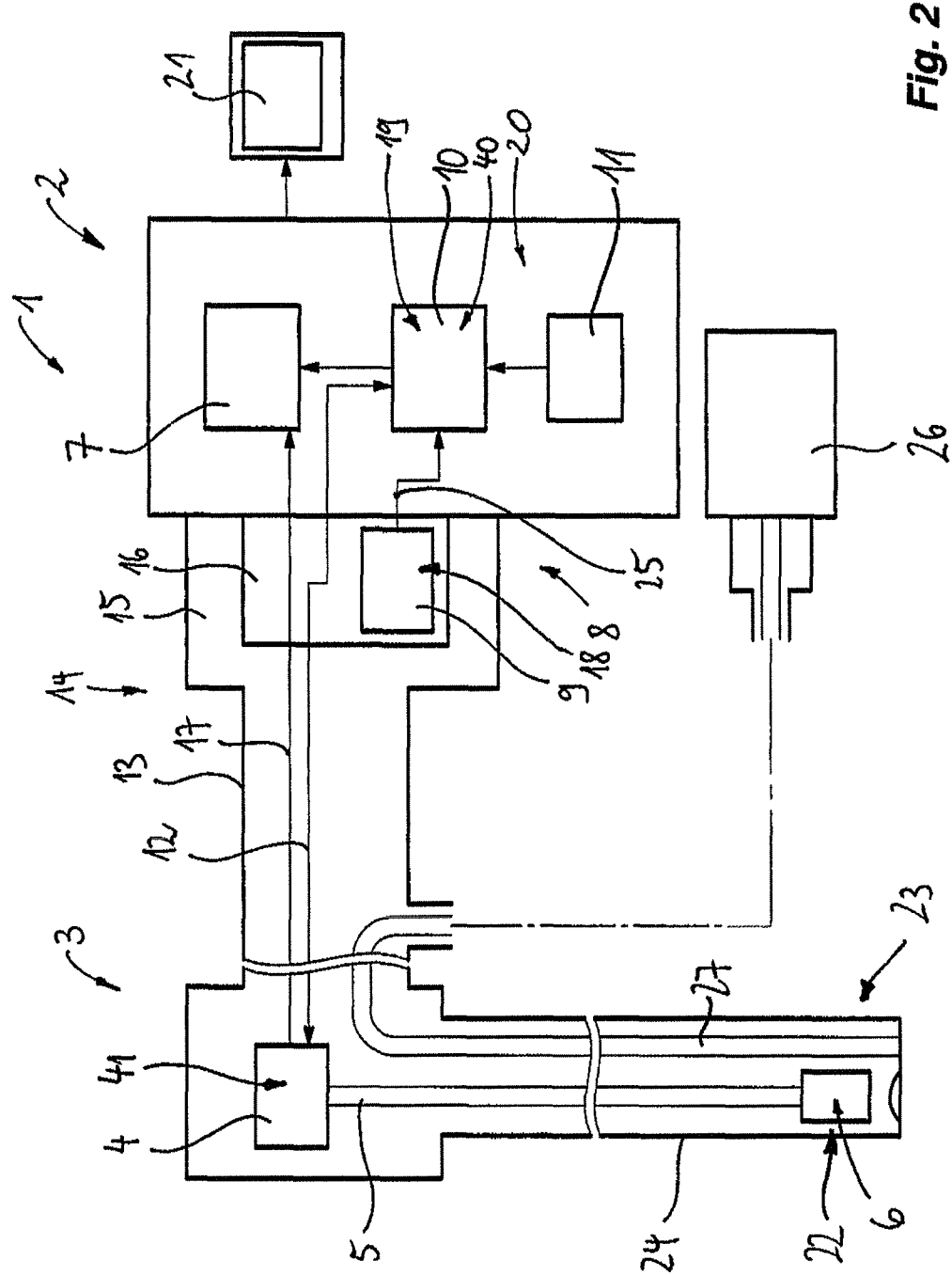
FIG. 2: shows a further image recording apparatus according to the invention, in which an image sensor is integrated in an endoscope tip.

FIG. 2 shows a further image recording apparatus 1 according to the invention. Components and functional units which are similar or identical in construction and/or functional terms to the previous exemplary embodiment have the same reference sign and are not described again. What was said with respect to FIG. 1 therefore applies correspondingly to FIG. 2.

The exemplary embodiment according to FIG. 2 differs from the exemplary embodiment according to FIG. 1 in that the image sensor 6 is not arranged in the camera head 3, but is arranged in an endoscope tip 23 of an endoscope shaft 24 as part of an opto-electrical assembly 22.

The exemplary embodiment according to FIG. 2 additionally differs from the exemplary embodiment according to FIG. 1 in that the storage device 9 is not read wirelessly, but in a wired-connected fashion.

To this end, the plug 16 and the camera control unit 2 have corresponding electrical connections 25.

If a camera control unit 2, which is identical to the camera control unit 2 according to FIG. 1, is used in the exemplary embodiment according to FIG. 2, the configuration unit 10 is thus set up for reading a connected storage device 9 in wire-connected and wireless fashion.

The exemplary embodiment according to FIG. 2 furthermore differs from the exemplary embodiment according to FIG. 1 in that a light source 26 is connectable to a waveguide 27 of the endoscope shaft 24 so as to illuminate an examination area. This connection can—as shown—be realized at the connecting cable 13 or—in another exemplary embodiment—at the endoscope shaft 24.

In the exemplary embodiment according to FIG. 2, the camera head 3 is fixedly connected to the endoscope shaft 24. In further exemplary embodiments, the camera head 3 can be detachably connected to the endoscope shaft 24.

The camera control unit 2 from FIGS. 1 and 2 forms with the respective camera heads 3 from FIG. 1 and FIG. 2 an image recording apparatus set according to the invention. The camera head 3 from FIG. 2 is thus connectable to the camera control unit 2 from FIG. 1, and the camera 3 from FIG. 1 is connectable to the camera control unit 2 from FIG. 2.

Figure 3:
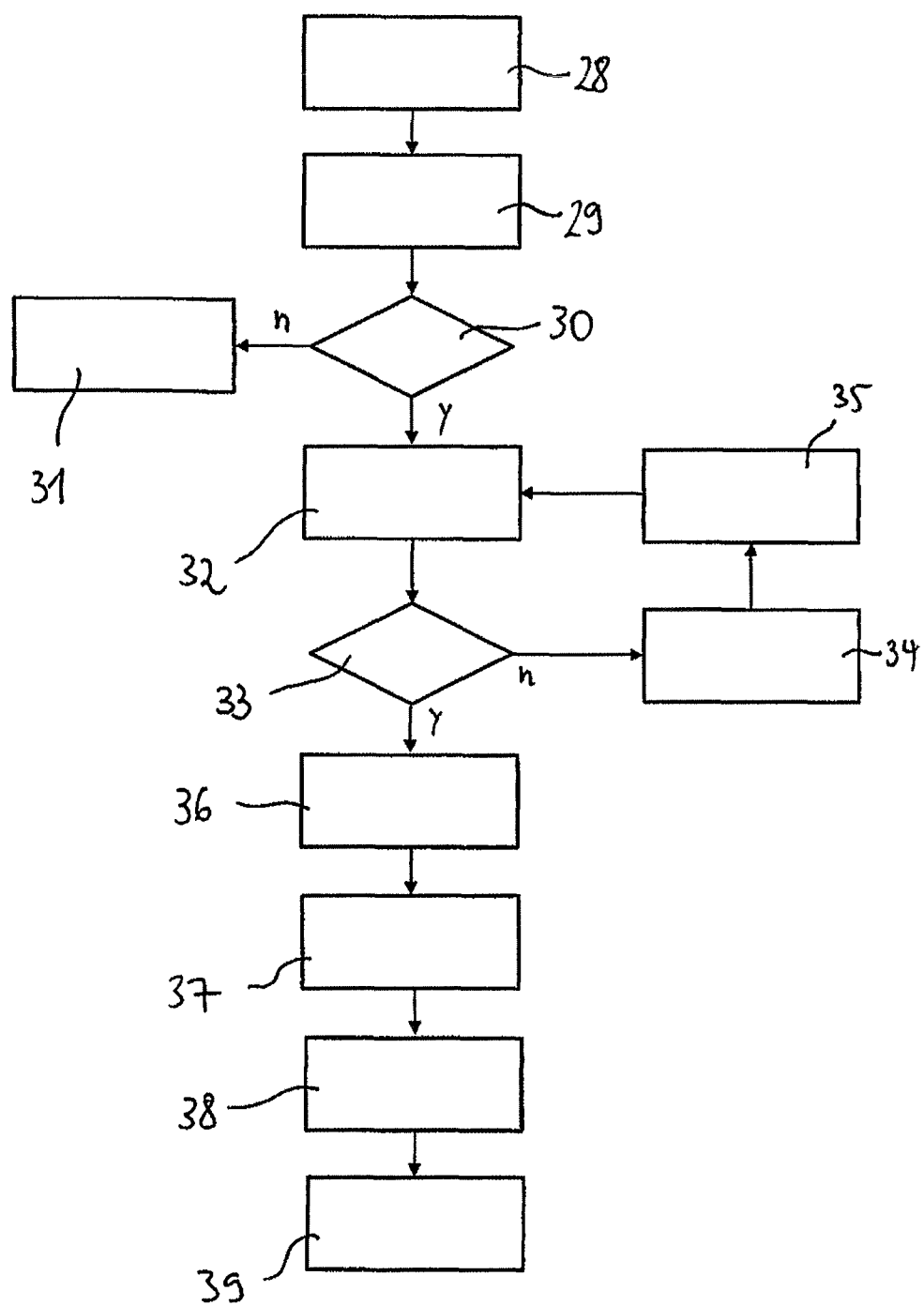
FIG. 3: shows a flowchart of a method according to the invention.

FIG. 3 shows a flowchart of a method according to the invention.

Here, first the camera head 3, for example the camera head 3 from FIG. 1 or the camera head from FIG. 2, is linked to the camera control unit 2 and connected thereto in a connecting step 28.

The configuration unit 10 then establishes a data link to the control device 9 so as to read camera-head-specific information in a read step 29.

In a camera-head-identification step 30, a check is carried out as to whether the camera head 3 is identifiable with the camera-head-specific information. If this is not the case (variant "n"), the method is terminated in a termination step and the user is informed accordingly.

If the camera head 3 is identified (alternative "y"), configuration data which are associated with the camera-head-specific information from the configuration data storage device 11 are read by the configuration unit 10 and transmitted to the image signal pre-processing unit 4 for configuration. The image signal pre-processing unit 4 is thus configured and provides for example a UART/RS-232 function.

A check is now carried out in a checking step 33 as to whether the configuration was successful. This can be done for example by checking the transmission channel 17 for transmission of video data (for example within 0.5 s). If this is not the case (alternative "n"), the camera head is switched off in a step 34 (for example by switching off the operating voltage), and the camera head 3 is switched on again in a step 35 (for example by switching on the operating voltage), and the method continues again with the configuration step 32.

If the configuration is successful (alternative "y"), normal operation of the camera head starts in a starting step 36, whereupon the remaining data for the camera head from the storage device 9 are read by the configuration unit 10 of the camera control unit 2 from the configuration data storage device 11 in a reading step 37. This can be, for example, geometry data of the endoscope or the image recording apparatus.

In an adjustment step 38, the camera control unit is adjusted with the remaining data, which is followed by normal operation 39.

It is provided to arrange in the image recording apparatus 1 a storage device 9 on a side of an interface 8 with a camera control unit 2 that faces a camera head 3 and to implement in the camera control unit 2 a configuration unit 10 with which camera-head-specific information is readable from the storage device 9 and transmittable to an image signal pre-processing unit 4 of the camera head 3 for configuration.

LIST OF REFERENCES 1 image recording apparatus
2 camera control unit
3 camera head
4 image signal pre-processing unit
5 electrical signal
6 image sensor
7 image signal processing unit
8 interface
9 storage device
10 configuration unit
11 configuration data storage device
12 data link
13 connecting cable
14 end of 13
15 connection
16 plug
17 transmission channel
18 RFID transponder
19 RFID reader
20 updating means
21 monitor
22 opto-electrical assembly
23 endoscope tip
24 endoscope shaft
25 electrical connection
26 light source
27 waveguide
28 connecting step
29 reading step
30 camera head identification step
31 termination step
32 configuration step
33 checking step
34 step
35 step
36 start step
37 reading step
38 adjustment step
39 normal operation
40 microprocessor
41 FPGA unit

The invention claimed is:

1. An image recording apparatus comprising:
a camera control unit and a camera head,
the camera head including an image signal pre-processing unit for generating an image signal stream, and
the camera control unit has an image signal processing unit,
wherein the camera head is releasably connectable to the image signal processing unit via an interface for transmitting the image signal stream,
a storage device of the camera head that contains camera-head-specific information is connectable via the interface to a configuration unit in the camera control unit, and
the configuration unit is set up
for receiving the camera-head-specific information from the connected storage device and
for reading configuration data for configuring the image signal pre-processing unit, corresponding to the camera-head-specific information, from a configuration data storage device of the camera control unit,
wherein the configuration data is updated and modified independently of the camera head, and for writing the configuration data to the image signal pre-processing unit,
the camera control unit is set up for configuring the image signal pre-processing unit with the configuration data, and
the image signal pre-processing unit is or comprises an FPGA unit or a combination of an FPGA unit and a microcontroller.

2. An image recording apparatus comprising:
a camera control unit and a camera head,
the camera head including an image signal pre-processing unit for generating an image signal stream, and
the camera control unit has an image signal processing unit,
wherein the camera head is releasably connectable to the image signal processing unit via an interface for transmitting the image signal stream, a storage device of the camera head that contains camera-head-specific information is connectable via the interface to a configuration unit in the camera control unit, and the configuration unit is set up for receiving the camera-head-specific information from the connected storage device and for reading configuration data for configuring the image signal pre-processing unit, corresponding to the camera-head-specific information, from a configuration data storage device of the camera control unit, wherein the configuration data is updated and modified independently of the camera head, and for writing the configuration data to the image signal pre-processing unit, the camera control unit is set up for configuring the image signal pre-processing unit with the configuration data, the image signal pre-processing unit is or comprises an FPGA unit or a combination of an FPGA unit and a microcontroller, the interface is implemented at a connecting cable, and the storage device is arranged at or in a connection of the interface, wherein the connection is implemented at a plug permitting connection via the interface, and the plug is implemented at an end of the connecting cable that faces the camera control unit.

3. The image recording apparatus as claimed in claim 1, wherein the storage device is readable in at least one of a wire-connected or a wireless fashion.

4. The image recording apparatus as claimed in claim 3, wherein the storage device has an RFID transponder.

5. The image recording apparatus as claimed in claim 1, wherein the configuration data comprises at least one of a look-up table or at least one short code.

6. A method for configuring a camera head of an image recording apparatus, comprising connecting a camera control unit to the camera head and reading camera-head-specific information from a storage device of the camera head, reading configuration data for configuring the image signal pre-processing unit corresponding to the camera-head-specific information from a configuration data storage device of the camera control unit, wherein the configuration data is updated and modified independently from the camera head, transmitting the configuration data to the camera head, using the configuration data for setting up an image signal pre-processing unit in the camera head, reading the configuration data with a configuration unit of the camera control unit and transmitting the configuration data to the camera head, and the configuration unit writing the configuration data to the image signal pre-processing unit, wherein the image signal pre-processing unit is or comprises an FPGA unit or a combination of an FPGA unit and a microcontroller.

7. The method of claim 6, wherein the camera-head specific information is read in at least one of a wire-connected or wireless fashion.

8. The method as claimed in claim 6, further comprising using at least one of a look-up table as the configuration data or at least one short code.

9. The method as claimed in claim 6, further comprising updating the configuration data in the configuration storage device.

10. The method as claimed in claim 6, wherein the image signal pre-processing unit has an FPGA unit, a microcontroller, and a CPLD unit, or a combination of an FPGA unit and a microcontroller.

11. An image recording apparatus set having a camera control unit and at least two camera heads, wherein the camera control unit forms with each of the at least two camera heads an image recording apparatus as claimed in claim 1.

12. The image recording apparatus as claimed in claim 1, wherein a plug and the camera control unit have corresponding electrical connections, wherein the storage device is read via a wired connection.

13. The image recording apparatus as claimed in claim 2, wherein the plug and the camera control unit have corresponding electrical connections, wherein the storage device is read via a wired connection.

* * * * *